United States Patent
Riestenberg et al.

(10) Patent No.: US 10,743,901 B2
(45) Date of Patent: Aug. 18, 2020

(54) SNAP FIT CLAMP PAD FOR ULTRASONIC SURGICAL INSTRUMENT

(71) Applicant: Ethicon Endo-Surgery, LLC, Guaynabo, PR (US)

(72) Inventors: Paul F. Riestenberg, North Bend, OH (US); David Sepulveda-Leyva, South Lebanon, OH (US); Benjamin D. Dickerson, Cincinnati, OH (US); Craig N. Faller, Batavia, OH (US)

(73) Assignee: Ethicon LLC, Guaynabo, PR (US)

( * ) Notice: Subject to any disclaimer, the term of this patent is extended or adjusted under 35 U.S.C. 154(b) by 982 days.

(21) Appl. No.: 14/982,129

(22) Filed: Dec. 29, 2015

(65) Prior Publication Data
US 2017/0181765 A1    Jun. 29, 2017

(51) Int. Cl.
*A61B 17/32* (2006.01)
*A61B 17/28* (2006.01)
*A61B 17/29* (2006.01)
*A61B 17/00* (2006.01)

(52) U.S. Cl.
CPC ...... *A61B 17/320068* (2013.01); *A61B 17/28* (2013.01); *A61B 17/29* (2013.01); *A61B 17/320092* (2013.01); *A61B 2017/0046* (2013.01); *A61B 2017/00353* (2013.01); *A61B 2017/00477* (2013.01); *A61B 2017/2825* (2013.01); *A61B 2017/2926* (2013.01); *A61B 2017/2945* (2013.01); *A61B 2017/320071* (2017.08); *A61B 2017/320078* (2017.08);
(Continued)

(58) Field of Classification Search
CPC . A61B 17/320068; A61B 17/29; A61B 17/28; A61B 17/320092; A61B 2017/0046; A61B 2017/2926; A61B 2017/2945; A61B 2017/2825; A61B 2017/320094; A61B 2017/320095; A61B 2017/320071; A61B 2017/320078; A61B 2017/00353; A61B 2017/00477
See application file for complete search history.

(56) References Cited

U.S. PATENT DOCUMENTS

| | | |
|---|---|---|
| 5,322,055 A | 6/1994 | Davison et al. |
| 5,324,299 A | 6/1994 | Davison et al. |

(Continued)

FOREIGN PATENT DOCUMENTS

WO    WO 2000/078237 A1    12/2000

OTHER PUBLICATIONS

U.S. Appl. No. 14/553,378, filed Nov. 25, 2014.
(Continued)

*Primary Examiner* — Erich G Herbermann
(74) *Attorney, Agent, or Firm* — Frost Brown Todd LLC

(57) ABSTRACT

An ultrasonic instrument includes a shaft assembly and an end effector having an ultrasonic blade, a clamp arm, and a clamp pad. The clamp arm is pivotally coupled with the shaft assembly. The clamp pad is configured to removably couple with the clamp arm while the clamp arm is pivotally coupled to the shaft assembly. The clamp arm includes a mortise and a pair of support gussets. The clamp pad includes a tenon and a pair of resilient projections where the tenon engages the mortise of the clamp arm and the projections contact the support gussets of the clamp arm.

19 Claims, 10 Drawing Sheets

(52) U.S. Cl.
CPC ............ *A61B 2017/320094* (2017.08); *A61B 2017/320095* (2017.08)

(56) References Cited

U.S. PATENT DOCUMENTS

| | | | |
|---|---|---|---|
| 5,810,881 A * | 9/1998 | Hoskin | A61B 17/062 269/275 |
| 5,873,873 A | 2/1999 | Smith et al. | |
| 5,980,510 A | 11/1999 | Tsonton et al. | |
| 6,254,623 B1 | 7/2001 | Haibel, Jr. et al. | |
| 6,283,981 B1 | 9/2001 | Beaupre | |
| 6,309,400 B2 | 10/2001 | Beaupre | |
| 6,325,811 B1 | 12/2001 | Messerly | |
| 6,423,082 B1 | 7/2002 | Houser et al. | |
| 6,773,444 B2 | 8/2004 | Messerly | |
| 6,783,524 B2 | 8/2004 | Anderson et al. | |
| 7,544,200 B2 | 6/2009 | Houser et al. | |
| 8,057,498 B2 | 11/2011 | Robertson | |
| 8,461,744 B2 | 6/2013 | Wiener et al. | |
| 8,591,536 B2 | 11/2013 | Robertson | |
| 8,623,027 B2 | 1/2014 | Price et al. | |
| 8,911,460 B2 | 12/2014 | Neurohr et al. | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 2006/0079874 A1 * | 4/2006 | Faller | A61B 17/320092 606/40 |
| 2007/0011713 A1 | 1/2007 | Abramson et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2009/0099582 A1 | 4/2009 | Isaacs et al. | |
| 2012/0112687 A1 | 5/2012 | Houser et al. | |
| 2012/0116265 A1 | 5/2012 | Houser et al. | |
| 2012/0241503 A1 * | 9/2012 | Baxter, III | A61B 17/0643 227/176.1 |
| 2014/0005701 A1 | 1/2014 | Olson et al. | |
| 2015/0080924 A1 | 3/2015 | Stulen et al. | |
| 2015/0148834 A1 | 5/2015 | Gee et al. | |
| 2015/0164532 A1 | 6/2015 | Faller et al. | |
| 2015/0245850 A1 | 9/2015 | Hibner et al. | |

OTHER PUBLICATIONS

U.S. Appl. No. 61/410,603, filed Nov. 5, 2010.
International Search Report and Written Opinion dated May 4, 2017 for International Application No. PCT/US2016/0664476, 10 pages.
International Preliminary Report on Patentability dated Jul. 3, 2018 for International Application No. PCT/US2016/0664476, 7 pages.

* cited by examiner

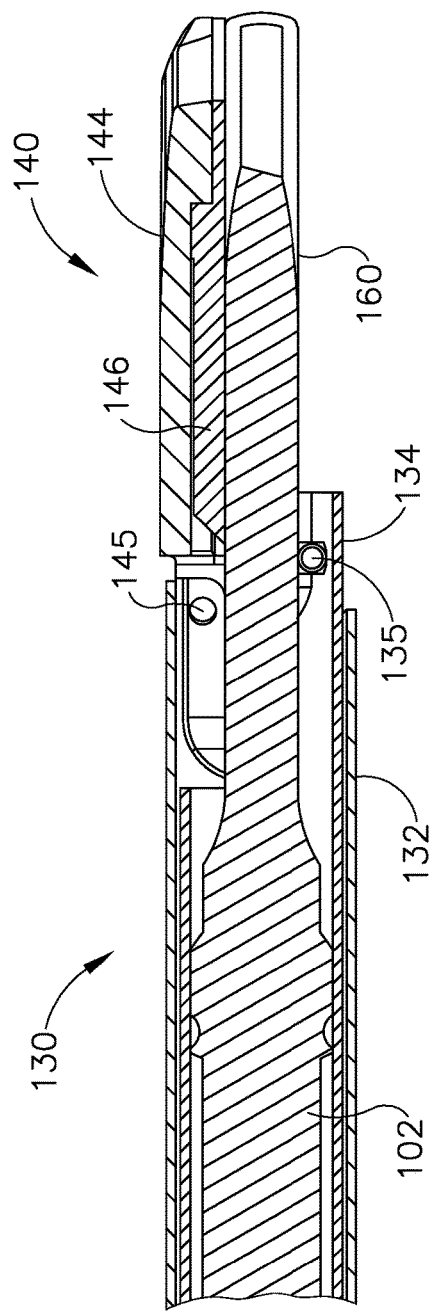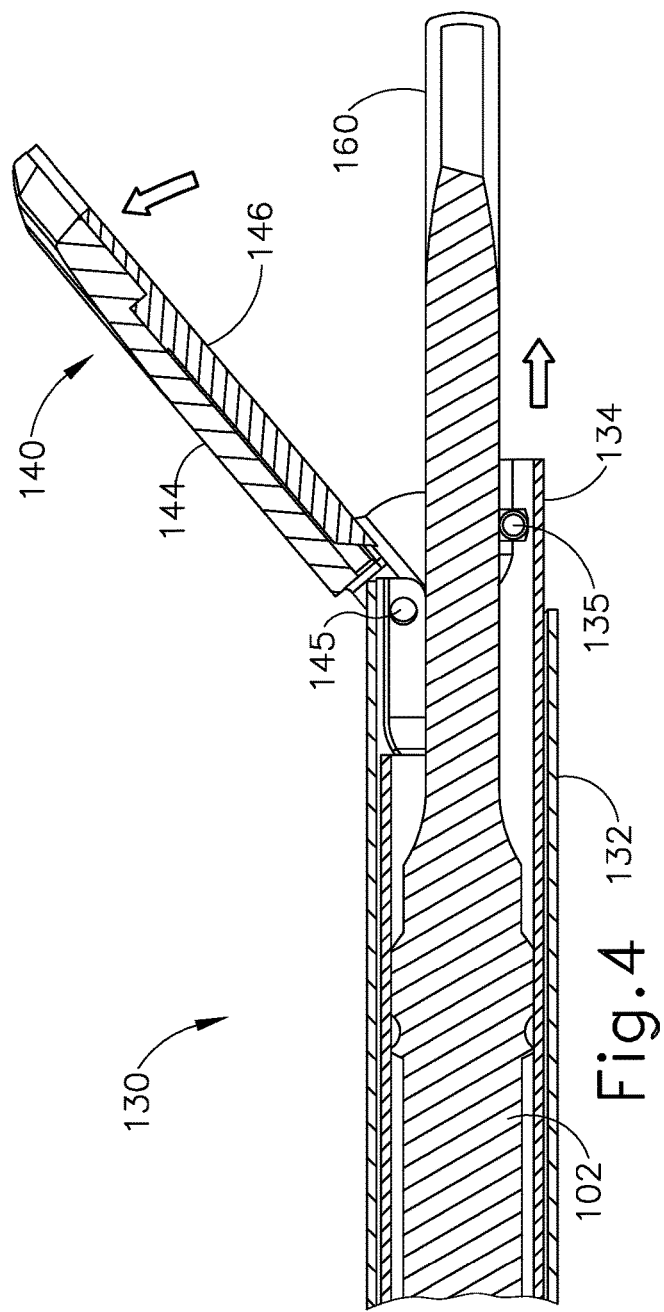

SNAP FIT CLAMP PAD FOR ULTRASONIC SURGICAL INSTRUMENT

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. Some instruments have a clamp arm and clamp pad for grasping tissue with the blade element.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Clamp pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2014, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; and U.S. Pub. No. 2014/0114334, published Apr. 24, 2014, issued as U.S. Pat. No. 9,095,367 on Aug. 4, 2015entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 3 depicts a cross-sectional side view of an end effector of the instrument of FIG. 2 in a closed position;

FIG. 4 depicts a cross-sectional side view of the end effector of FIG. 3 in an open position;

Figure 1:
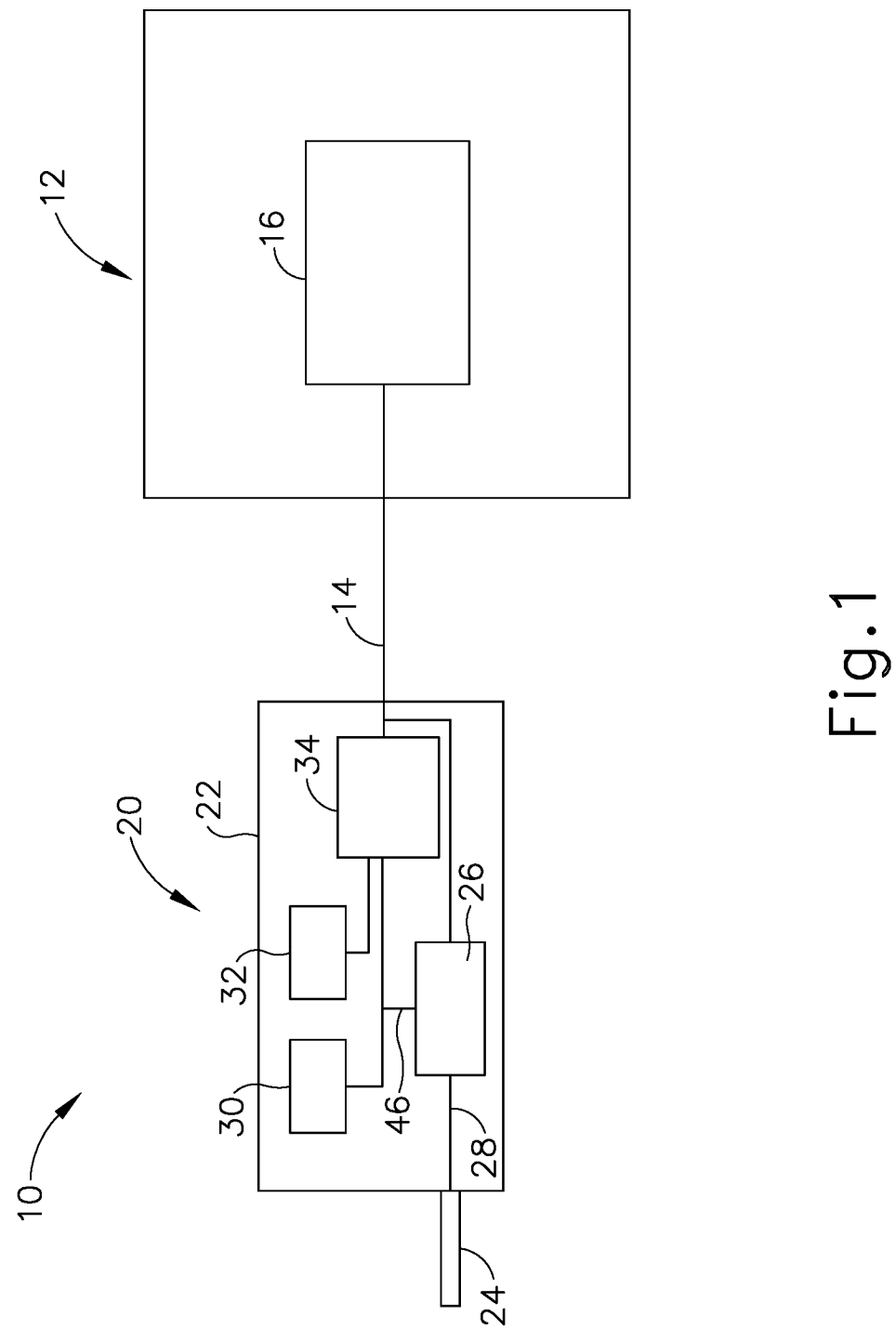
FIG. 1 depicts a block schematic view of an exemplary surgical system.
Figure 2:
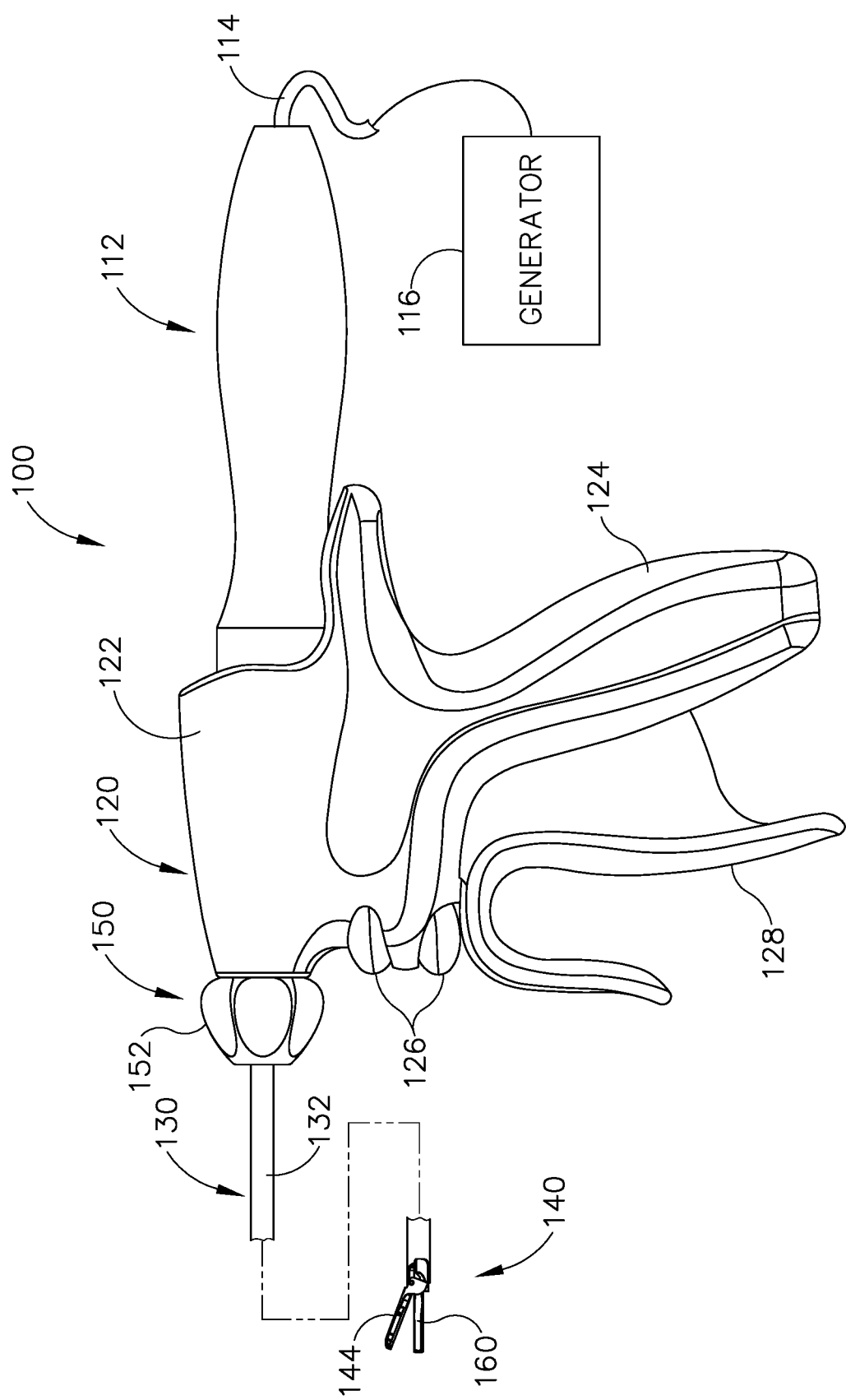
FIG. 2 depicts a side elevational view of an exemplary surgical instrument that may be incorporated into the system of FIG. 1.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04, GEN11, or GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handle assembly (22), which is configured to be grasped in one hand (or two hands) of an operator and manipulated by one hand (or two hands) of the operator during a surgical procedure. For instance, in some versions, handle assembly (22) may be grasped like a pencil by the operator. In some other versions, handle assembly (22) may include a scissor grip that may be grasped like scissors by the operator. In some other versions, handle assembly (22) may include a pistol grip that may be grasped like a pistol by the operator. Of course, handle assembly (22) may be configured to be gripped in any other suitable fashion. Furthermore, some versions of instrument (20) may substitute handle assembly (22) with a body that is coupled to a robotic surgical system that is configured to operate instrument (20) (e.g., via remote control, etc.). In the present example, a blade (24) extends distally from the handle assembly (22). Handle assembly (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handle assembly (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths ($n\lambda/2$). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handle assembly (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handle assembly (22). For instance, in some such versions, generator (12) only communicates one type of electrical power (e.g., just one voltage and/or current available) to handle assembly (22), and control circuitry (16) within handle assembly (22) is operable to modify the electrical power (e.g., the voltage of the electrical power), in accordance with selections made by the operator via control selector (30), before the electrical power reaches ultrasonic transducer (26). Furthermore, generator (12) may be incorporated into handle assembly (22) along with all other components of surgical system (10). For instance, one or more batteries (not shown) or other portable sources of power may be provided in handle assembly (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instrument

The following discussion relates to various exemplary components and configurations of instrument (20). It should be understood that the various examples of instrument (20) described below may be readily incorporated into surgical system (10) as described above. It should also be understood that the various components and operabilities of instrument (20) described above may be readily incorporated into the exemplary versions of instrument (20) described below. Various suitable ways in which the above and below teachings may be combined will be apparent to those of ordinary skill in the art in view of the teachings herein. It should also be understood that the below teachings may be readily combined with the various teachings of the references that are cited herein.

FIGS. 2-5 illustrate an exemplary ultrasonic surgical instrument (100). At least part of instrument (100) may be constructed and operable in accordance with at least some of the teachings of U.S. Pat. Nos. 5,322,055; 5,873,873; 5,980,510; 6,325,811; 6,773,444; 6,783,524; 8,461,744; 8,623,027; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2014/0114334, issued as U.S. Pat. No. 9,095,367 on Aug. 4, 2015; U.S. Pat. App. No. 61/410,603; and/or U.S. patent application Ser. No. 14/028,717, issued as U.S. Pat. No. 10,172,636 on Jan. 8, 2019. The disclosures of each of the foregoing patents, publications, and applications are incorporated by reference herein. As described therein and as will be described in greater detail below, instrument (100) is operable to cut tissue and seal or weld tissue (e.g., a blood vessel, etc.) substantially simultaneously. It should also be understood that instrument (100) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (100) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (100), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (100) of the present example comprises a handle assembly (120), a shaft assembly (130), and an end effector (140). Handle assembly (120) comprises a body (122) including a pistol grip (124) and a pair of buttons (126). Handle assembly (120) also includes a trigger (128) that is pivotable toward and away from pistol grip (124). It should be understood, however, that various other suitable configurations may be used, including but not limited to a pencil-grip configuration or a scissor-grip configuration. End effector (140) includes an ultrasonic blade (160) and a pivoting clamp arm (144). Clamp arm (144) is coupled with trigger (128) such that clamp arm (144) is pivotable toward ultrasonic blade (160) in response to pivoting of trigger (128) toward pistol grip (124); and such that clamp arm (144) is pivotable away from ultrasonic blade (160) in response to pivoting of trigger (128) away from pistol grip (124). Various suitable ways in which clamp arm (144) may be coupled with trigger (128) will be apparent to those of ordinary skill in the art in view of the teachings herein. In some versions, one or more resilient members are used to bias clamp arm (144) and/or trigger (128) to the open position shown in FIG. 4.

An ultrasonic transducer assembly (112) extends proximally from body (122) of handle assembly (120). Transducer assembly (112) is coupled with a generator (116) via a cable (114). Transducer assembly (112) receives electrical power from generator (116) and converts that power into ultrasonic vibrations through piezoelectric principles. Generator (116) may include a power source and control module that is configured to provide a power profile to transducer assembly (112) that is particularly suited for the generation of ultrasonic vibrations through transducer assembly (112). By way of example only, generator (116) may comprise a GEN 300 sold by Ethicon Endo-Surgery, Inc. of Cincinnati, Ohio. In addition or in the alternative, generator (116) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

Blade (160) of the present example is operable to vibrate at ultrasonic frequencies in order to effectively cut through and seal tissue, particularly when the tissue is being clamped between clamp arm (144) and blade (160). Blade (160) is positioned at the distal end of an acoustic drivetrain. This acoustic drivetrain includes transducer assembly (112) and an acoustic waveguide (102). Transducer assembly (112) includes a set of piezoelectric discs (not shown) located proximal to a horn (not shown) of rigid acoustic waveguide (102). The piezoelectric discs are operable to convert electrical power into ultrasonic vibrations, which are then transmitted along acoustic waveguide (102), which extends through shaft assembly (130), to blade (160) in accordance with known configurations and techniques. By way of example only, this portion of the acoustic drivetrain may be configured in accordance with various teachings of various references that are cited herein.

Waveguide (102) is secured within shaft assembly (130) via a pin (133), which passes through waveguide (102) and shaft assembly (130). Pin (133) is located at a position along the length of waveguide (102) corresponding to a node associated with resonant ultrasonic vibrations communicated through waveguide (102). When ultrasonic blade (160) is in an activated state (i.e., vibrating ultrasonically), ultrasonic blade (160) is operable to effectively cut through and seal tissue, particularly when the tissue is being clamped between clamp arm (144) and ultrasonic blade (160). It should be understood that waveguide (102) may be configured to amplify mechanical vibrations transmitted through waveguide (102). Furthermore, waveguide (102) may include features operable to control the gain of the longitudinal vibrations along waveguide (102) and/or features to tune waveguide (102) to the resonant frequency of the system.

In the present example, the distal end of blade (160) is located at a position corresponding to an anti-node associated with resonant ultrasonic vibrations communicated through waveguide (102), in order to tune the acoustic assembly to a preferred resonant frequency $f_o$ when the acoustic assembly is not loaded by tissue. When transducer assembly (112) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (112) of the present example is activated, these mechanical oscillations are transmitted through waveguide (102) to reach blade (160), thereby providing oscillation of blade (160) at the resonant ultrasonic frequency. Thus, when tissue is secured between blade (160) and clamp arm (144), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (144) to also cauterize the tissue. While some configurations for an acoustic transmission assembly and transducer assembly (112) have been described, still other suitable configurations for an acoustic transmission assembly and transducer assembly (112) will be apparent to one or ordinary skill in the art in view of the teachings herein. Similarly, other suitable configurations for end effector (140) will be apparent to those of ordinary skill in the art in view of the teachings herein.

An operator may activate buttons (126) to selectively activate transducer assembly (112) to activate blade (160). In the present example, two buttons (126) are provided—one for activating blade (160) at a low power and another for activating blade (160) at a high power. However, it should be understood that any other suitable number of buttons and/or otherwise selectable power levels may be provided. For instance, a foot pedal may be provided to selectively activate transducer assembly (112). Buttons (126) of the present example are positioned such that an operator may readily fully operate instrument (100) with a single hand. For instance, the operator may position their thumb about pistol grip (124), position their middle, ring, and/or little finger about trigger (128), and manipulate buttons (126) using their index finger. Of course, any other suitable techniques may be used to grip and operate instrument (100); and buttons (126) may be located at any other suitable positions.

Shaft assembly (130) of the present example comprises an outer sheath (132), an inner tube (134) slidably disposed within outer sheath (132), and a waveguide (102) disposed within inner tube (134). As will be discussed in more detail below inner tube (134) is operable to translate longitudinally within outer sheath (132) relative to outer sheath (132) to selectively pivot clamp arm (144) toward and away from blade (160). Shaft assembly (130) of the present example further includes a rotation assembly (150). Rotation assembly (150) is operable to rotate the entire shaft assembly (130) and end effector (140) relative to handle assembly (120) about a longitudinal axis of shaft assembly (130). In some versions, rotation assembly (150) is operable to selectively lock the angular position of shaft assembly (130) and end effector (140) relative to handle assembly (120) about the longitudinal axis of shaft assembly (130). For instance, a rotation knob (152) of rotation assembly (150) may be translatable between a first longitudinal position, in which shaft assembly (130) and end effector (140) are rotatable relative to handle assembly (120) about the longitudinal axis of shaft assembly (130); and a second longitudinal position, in which shaft assembly (130) and end effector (140) are not rotatable relative to handle assembly (120) about the longitudinal axis of shaft assembly (130). Of course, shaft assembly (130) may have a variety of other components, features, and operabilities, in addition to or in lieu of any of those noted above. Other suitable configurations for shaft assembly (130) will be apparent to those of ordinary skill in the art in view of the teachings herein.

As shown in FIGS. 3 and 4, end effector (140) includes ultrasonic blade (160) and clamp arm (144). Clamp arm (144) includes a clamp pad (146) secured to an underside of clamp arm (144), facing blade (160). Clamp arm (144) is pivotably coupled with a distal end of outer sheath (132) of shaft assembly (130) above ultrasonic blade (160) via a pin (145). As best seen in FIG. 4, a distal end of inner tube (134)

is rotatably coupled with a proximal end of clamp arm (144) below ultrasonic blade (160) via a pin (135) such that longitudinal translation of inner tube (134) causes rotation of clamp arm (144) about pin (145) toward and away from ultrasonic blade (160) to thereby clamp tissue between clamp arm (144) and ultrasonic blade (160) to cut and/or seal the tissue. In particular, proximal longitudinal translation of inner tube (134) relative to outer sheath (132) and handle assembly (120) causes clamp arm (144) to move toward ultrasonic blade (160); and distal longitudinal translation of inner tube (134) relative to outer sheath (132) and handle assembly (120) causes clamp arm (144) to move away from ultrasonic blade (160).

Figure 5:
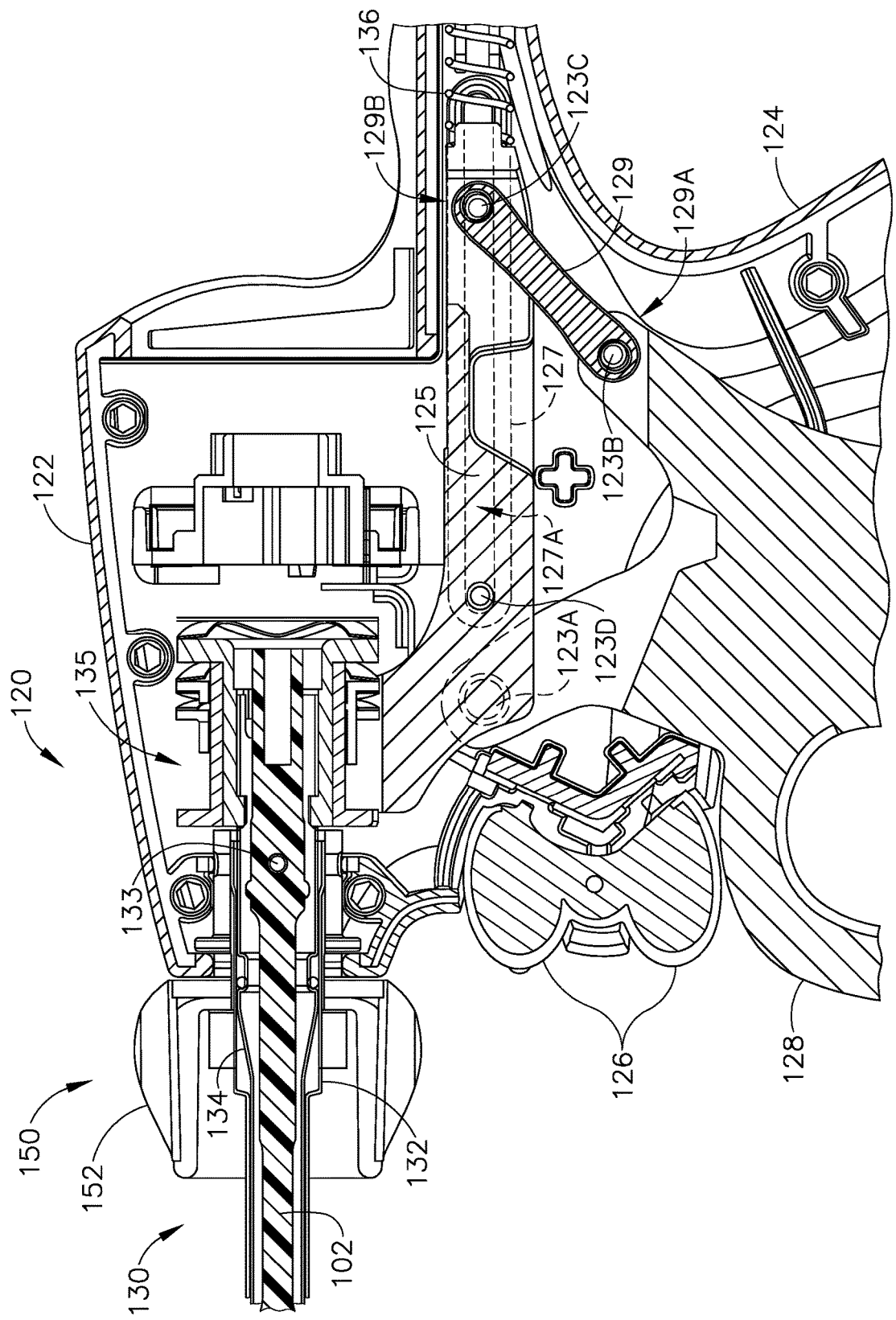
FIG. 5 depicts a cross-sectional side view of a handle assembly of the instrument of FIG. 2.

As shown in FIG. 5, and as discussed above, trigger (128) is pivotably coupled to handle assembly (120) via a pin (123A) such that trigger (128) is operable to rotate about pin (123A). As will be described in more detail below, trigger (128) is coupled with a yoke (125) via a linkage (129) such that rotation of trigger (128) about pin (123A) causes longitudinal translation of yoke (125). A first end (129A) of linkage (129) is rotatably coupled with a proximal portion of trigger (128) via a pin (123B). A second end (129B) of linkage (129) is rotatably coupled with a proximal portion of yoke (125) via a pin (123C). A pair of elongate oval-shaped projections (127) extend inwardly from interior surfaces of body (122). An interior surface of each oval-shaped projection (127) defines an elongate oval-shaped slot (127A). Pin (123C) passes completely through the proximal portion of yoke (125) and second end (129B) of linkage (129) such that ends of pin (123C) extend from opposite sides of yoke (125). These ends of pin (123C) are slidably and rotatably disposed within oval-shaped slots (127A). A pin (123D) passes completely through a distal portion of yoke (125) such that ends of pin (123D) extend from opposite sides of yoke (125). These ends of pin (123D) are slidably and rotatably disposed within oval-shaped slots (127A). It should therefore be understood that yoke (125) is longitudinally translatable within oval-shaped slots (127A) via pins (123C, 123D) between a proximal longitudinal position and a distal longitudinal position. Furthermore, because the proximal portion of trigger (128) is coupled with yoke (125) via linkage (129), pivoting of trigger (128) toward and away from pistol grip (124) will cause longitudinal translation of yoke (125) within oval-shaped slots (127A). In particular, pivoting of trigger (128) toward pistol grip (124) will cause proximal longitudinal translation of yoke (125) within oval-shaped slots (127A); and that pivoting of trigger (128) away from pistol grip (124) will cause distal longitudinal translation of yoke (125) within oval-shaped slots (127A).

A distal portion of yoke (125) is coupled with inner tube (134) of shaft assembly (130) via a coupling assembly (135). As discussed above, inner tube (134) is longitudinally translatable within outer sheath (132), such that inner tube (134) is configured to longitudinally translate concurrently with yoke (125). Furthermore, because pivoting of trigger (128) toward pistol grip (124) causes proximal longitudinal translation of yoke (125), it should be understood that pivoting of trigger (128) toward pistol grip (124) will cause proximal longitudinal translation of inner tube (134) relative to outer sheath (132) and handle assembly (120); and because pivoting of trigger (128) away from pistol grip (124) causes distal longitudinal translation of yoke (125), it should be understood that and that pivoting of trigger (128) away from pistol grip (124) will cause distal longitudinal translation of inner tube (134) relative to outer sheath (132) and handle assembly (120). Finally, because longitudinal translation of inner tube (134) causes rotation of clamp arm (144) toward and away from blade (160) as discussed above, it should be understood that pivoting of trigger (128) toward pistol grip (124) will cause clamp arm (144) to move toward ultrasonic blade (160); and that pivoting of trigger (128) away from pistol grip (124) will cause clamp arm (144) to move away from ultrasonic blade (160).

In some versions, one or more resilient members are used to bias clamp arm (144) and/or trigger (128) to the open position shown in FIG. 4. For instance, as shown in FIG. 5, a spring (136) is positioned within a proximal end of body (122) of handle assembly (120). Spring (136) bears against body (122) and a proximal end of yoke (125) to thereby bias yoke (125) toward the distal position. Biasing of yoke (125) toward the distal position causes inner tube (134) to be biased distally and further causes trigger (128) to be biased away from pistol grip (124).

The foregoing components and operabilities of instrument (100) are merely illustrative. Instrument (100) may be configured in numerous other ways as will be apparent to those of ordinary skill in the art in view of the teachings herein. By way of example only, at least part of instrument (100) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940,now abandoned; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 5, 2016; U.S. Pub. No. 2012/0112687; U.S. Pub. No. 2012/0116265, now abandoned; U.S. Pub. No. 2014/0005701, issued as U.S. Pat. No. 9,393,037 on Jul. 19, 2016; and/or U.S. Pub. No. 2014/0114334, issued as U.S. Pat. No. 9,095,367 on Aug. 4, 2015. Additional merely illustrative variations for instrument (100) will be described in greater detail below. It should be understood that the below described variations may be readily applied to instrument (100) described above and any of the instruments referred to in any of the references that are cited herein, among others.

III. Exemplary Clamp Arm with Replaceable Clamp Pad

Those of ordinary skill in the art will recognize that clamp pad (146) may experience a substantial amount of wear and dear during use of end effector (140). For instance, clamp pad (146) may be formed of a polytetrafluoroethylene (PTFE) material. Clamp pad (146) may encounter heat, compression forces, and vibrations generated via blade (160), which may work together to eventually wear out the material forming clamp pad (146). It may therefore be desirable to provide a version of end effector (140) where clamp pad (146) is replaceable. In particular, it may be desirable to enable replacement of clamp pad (146) without necessarily also having to replace clamp arm (144) and/or other components of end effector (140).

Figure 6A:
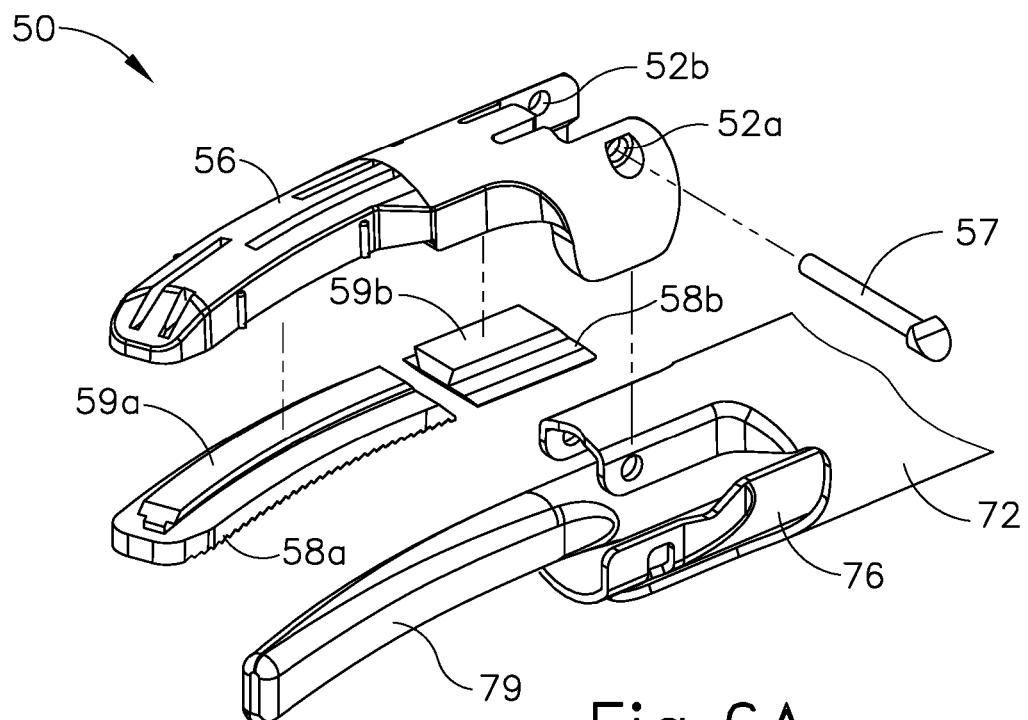
FIG. 6A depicts an exploded perspective view of an exemplary end effector that may be incorporated into the instrument of FIG. 2, with a clamp arm in a first position.
Figure 6B:
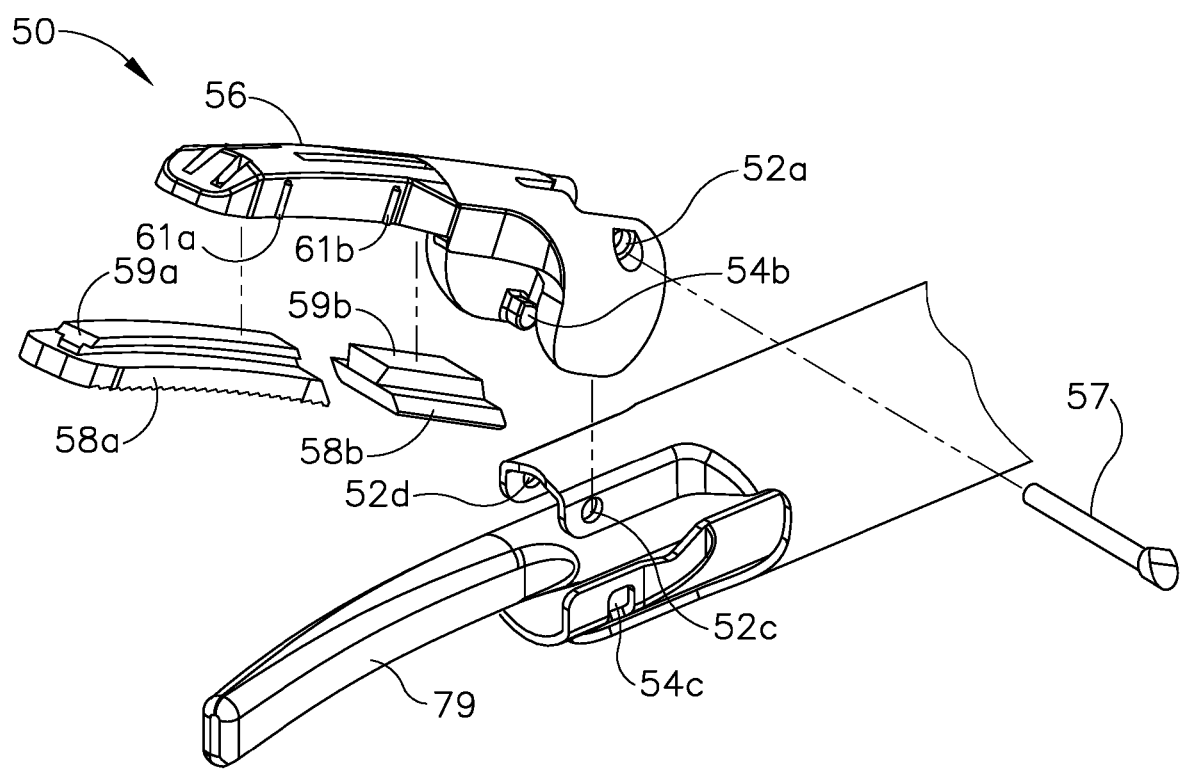
FIG. 6B depicts an exploded perspective view of the end effector of FIG. 6A, with the clamp arm in a second position.
Figure 7:
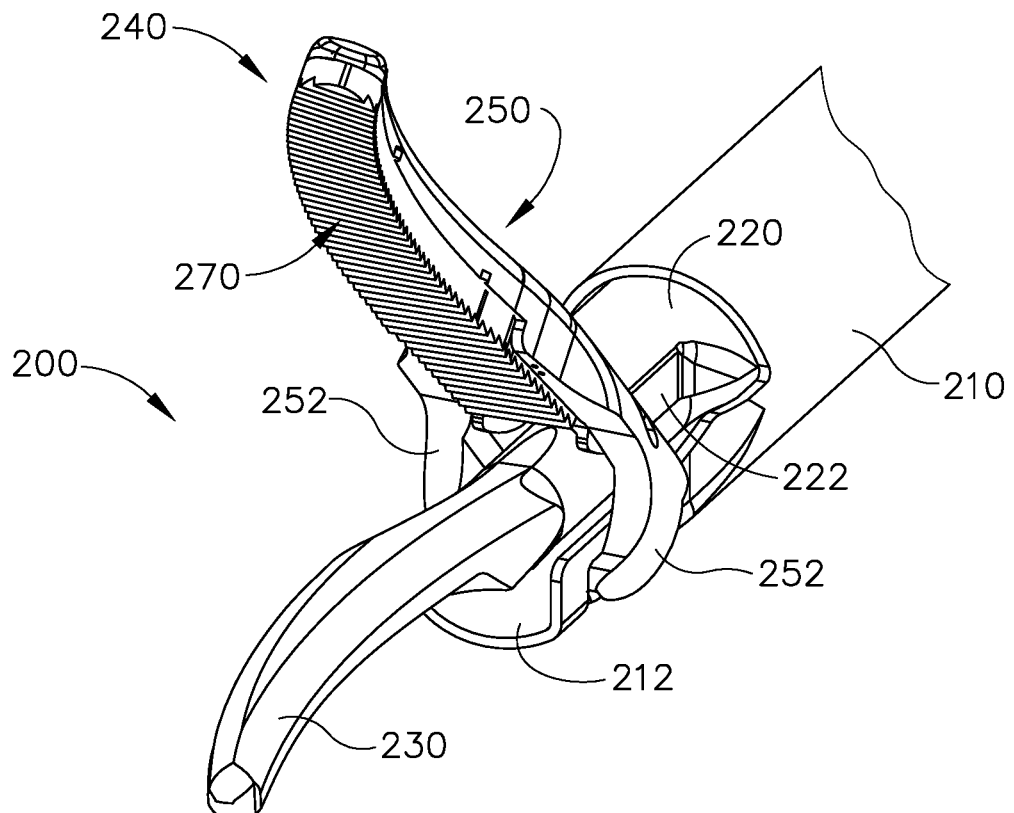
FIG. 7 depicts a perspective view from a distal end of an exemplary alternative end effector that may be incorporated into the instrument of FIG. 2, with the end effector in an open configuration.
Figure 8:
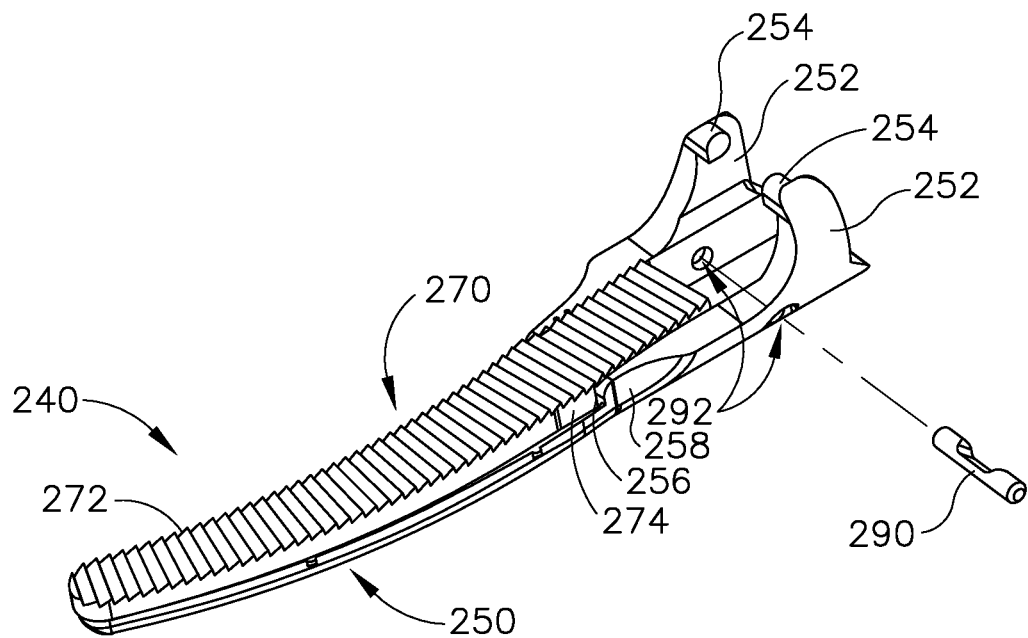
FIG. 8 depicts a partial perspective view of the end effector of FIG. 7 showing a clamp arm and clamp pad with a pin.

FIGS. 6A-B show an exemplary end effector (50) with a detachable clamp arm (56) and replaceable clamp pads (58a, 58b). End effector (50) may be readily incorporated into ultrasonic instrument (20, 100) described above. End effector (50) further includes an outer sheath (72), an inner tube (76), an ultrasonic blade (79), and a pivot pin (57). Outer sheath (72), inner tube (76), and blade (79) are substantially similar to outer sheath (132), inner tube (134) and ultrasonic blade (160), respectively, discussed above.

Detachable clamp arm (56) includes coupling holes (52a, 52b) that are configured to receive pivot pin (57). Clamp arm (56) is pivotally coupled to outer sheath (72) via pivot pin (57). Clamp arm (56) is pivotally coupled to inner sheath (76) via integral studs (54b), which are disposed in openings (54c) of inner sheath (76). Clamp pads (58a, 58b) further include tapered tenons (59a, 59b) that are configured to mate with complementary mortises (not shown) defined by detachable clamp arm (56). Tenons (59a, 59b) are configured to slide within mortises (not shown) at the proximal end of clamp arm (56) when clamp arm (56) is detached from outer sheath (72). Therefore, when clamp arm (56), with assembled clamp pads (58a, 58b), is attached to outer sheath (72) via pivot pin (57), pivot pin (57) prevents clamp pads (58a, 58b) from sliding proximally relative to clamp arm (56). In other words, pivot pin (57) and the closed distal end of clamp arm (56) confine clamp pads (58a, 58b) within the mortise via tenons (59a, 59b), with pivot pin (57) and the closed distal end of clamp arm (56) cooperating to act as longitudinal stops.

When detachable clamp arm (56) is assembled to outer sheath (72), clamp pads (58a, 58b) may be fixed relative to clamp arm (56). However, after a surgical procedure, clamp pads (58a, 58b) may be removed from detachable clamp arm (56) by removing pivot pin (57) to decouple clamp arm (56) and outer sheath (72). Once pivot pin (57) is removed from coupling holes (52a, 52b), clamp arm (56) may be removed from outer sheath (72), which enables clamp pads (58a, 58b) to slide relative to clamp arm (56) in the proximal direction. Used clamp pads (58a, 58b) may then be removed and replaced with new clamp pads (58a, 58b) with similar qualities. Then, assembled clamp arm (56) with new clamp pads (58a, 58b) may be coupled to outer sheath (72) via pivot pin (57), thereby fixing clamp pads (58a, 58b) relative to clamp arm (56). By way of example only, end effector (50) may be further constructed and operable in accordance with at least some of the teachings of U.S. Pat. No. 7,544,200, entitled "Combination Tissue Pad for Use with an Ultrasonic Surgical Instrument," issued Jun. 9, 2009, the disclosure of which is incorporated by reference herein.

IV. Exemplary Alternative Replaceable Clamp Pad Assembly

While end effector (50) allows for replacement of clamp pads (58a, 58b), end effector (50) requires removal of clamp arm (56) from outer sheath (72) in order to replace clamp pads (58a, 58b). In some instances, it may be desirable to allow for replacement of a clamp pad (58a, 58b, 146) from a clamp arm (56, 144) without having to first remove the clamp arm (56, 144) from anything. Providing replacement of a clamp pad (58a, 58b, 146) from a clamp arm (56, 144) without having to first remove the clamp arm (56, 144) from anything may simplify the process of sterilizing the instrument (20, 100), thereby saving time and/or costs associated with replacing clamp pad (58a, 58b, 146). The following examples relate to various alternative clamp arm and clamp pad configurations that may be used to provide replacement of the clamp pad without having to first remove the clamp arm from anything else. It should be understood that the following examples may be readily incorporated into end effectors (50, 140). It should also be understood that the following examples are merely illustrative.

In any of the examples described below, instrument (100) may be further modified in accordance with at least some of the teachings of U.S. patent application Ser. No. 14/623,812, entitled "Ultrasonic Surgical Instrument with Removable Handle Assembly," filed Feb. 17, 2015, issued as U.S. Pat. No. 10,010,340 on Jul. 3, 2018, the disclosure of which is incorporated by reference herein. For instance, instrument (100) may be modified to enable clamp arm (144) to be hyperextended to pivot wider than the open position shown in FIG. 4, as disclosed in U.S. patent application Ser. No. 14/623,812 (see, e.g., FIGS. 36A-36B and associated text of U.S. patent application Ser. No. 14/623,812), issued as U.S. Pat. No. 10,010,340 on Jul. 3, 2018. Such hyperextension of clamp arm (144) may provide easier access to clamp pad (146) and thereby further facilitate replacement of clamp pad (146).

In addition or in the alternative, in any of the examples described below, instrument (100) may be further modified in accordance with at least some of the teachings of U.S. patent application Ser. No. 14/553,378, entitled "Ultrasonic Surgical Instrument with Blade Cooling through Retraction," filed Nov. 25, 2014, issued as U.S. Pat. No. 10,433,863 on Oct. 8, 2019the disclosure of which is incorporated by reference herein. For instance, instrument (100) may be modified to enable blade (160) to be retracted proximally from the position shown in FIG. 4, as disclosed in U.S. patent application Ser. No. 14/553,378 (see, e.g., FIGS. 20A-20B and associated text of U.S. patent application Ser. No. 14/553,378), issued as U.S. Pat. No. 10,433,863 on Oct. 8, 2019. Such retraction of blade (160) may also provide easier access to clamp pad (146) and thereby further facilitate replacement of clamp pad (146) in accordance with the teachings below.

As yet another merely illustrative example, the various teachings below may be combined with the various teachings of U.S. patent application Ser. No. 14/552,614, entitled "Ultrasonic Surgical Instrument with Staged Clamping," filed Nov. 25, 2014, issued as U.S. Pat. No. 10,004,527 on Jun. 26, 2018, the disclosure of which is incorporated by reference herein. It should be understood that a replaceable clamp pad (146) may have various kinds of features that may fit into grooves of a clamp arm (144) and/or otherwise fit with features of a clamp arm (144). Various suitable ways in which the below teachings may be implemented into various kinds of instruments (100) will be apparent to those of ordinary skill in the art.

FIGS. 7-9B show an exemplary alternative end effector (200), or portions thereof. End effector (200) may be readily incorporated into ultrasonic instrument (20, 100) described above. End effector (200) of this example includes an ultrasonic blade (230) and a clamp arm assembly (240). Clamp arm assembly (240) includes a clamp arm (250) and a clamp pad (270) secured to an underside of clamp arm (250). End effector (200) is positioned at the end of a shaft assembly that includes an outer sheath (210) and an inner tube (220). Outer sheath (210), inner tube (220), and blade (230) are substantially similar to outer sheath (132, 72), inner tube (134, 76) and ultrasonic blade (160, 79), respectively, discussed above.

Figure 9A:
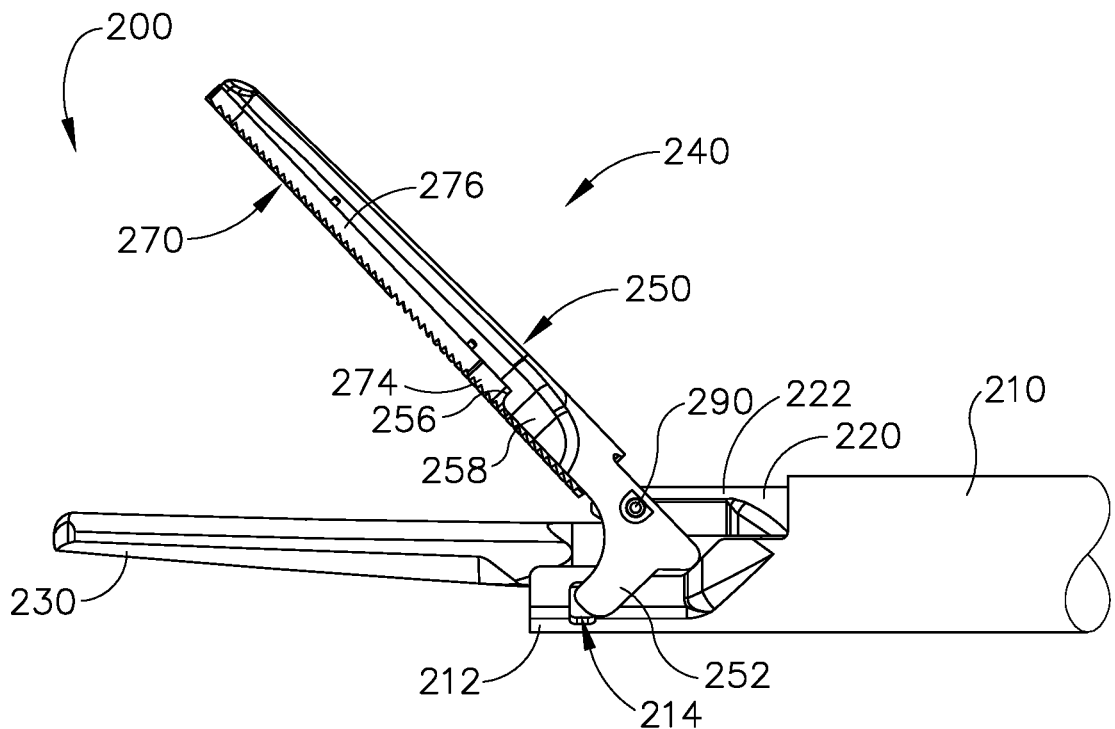
FIG. 9A depicts a side elevation view of the end effector of FIG. 7 in an open configuration.
Figure 9B:
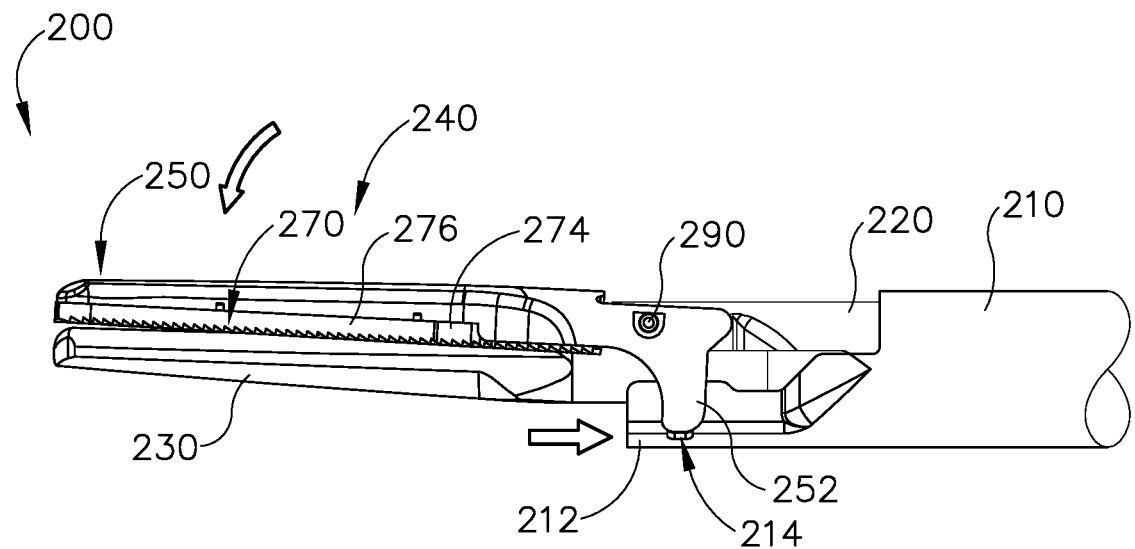
FIG. 9B depicts a side elevation view of the end effector of FIG. 9A in a closed configuration.

In the present example clamp arm (250) is pivotably coupled with a distal end (222) of inner tube (220) above ultrasonic blade (230) via coupling holes (292) of clamp arm (250) and a pivot pin (290). As best seen in FIGS. 9A-9B, a distal end (212) of outer sheath (210) is rotatably coupled with a proximal end (252) of clamp arm (250) below ultrasonic blade (230) via studs (254) of clamp arm (250) engaging with openings (214) in distal end (212) of outer sheath (210). In this way, longitudinal translation of outer sheath (210) relative to inner tube (220) causes rotation of clamp arm (250) about pin (290) toward and away from ultrasonic blade (230) to thereby clamp tissue between clamp arm (250) and ultrasonic blade (230) to cut and/or seal the tissue. In particular, proximal longitudinal translation of outer sheath (210) relative to inner tube (220) and handle assembly (120) causes clamp arm (250) to move toward ultrasonic blade (230); and distal longitudinal translation of outer sheath (210) relative to inner tube (220) and handle assembly (120) causes clamp arm (250) to move away from ultrasonic blade (230). In some alternative versions, inner tube (220) translates while outer sheath (210) remains stationary to provide pivotal movement of clamp arm (250) toward and away from ultrasonic blade (230).

Figure 10:
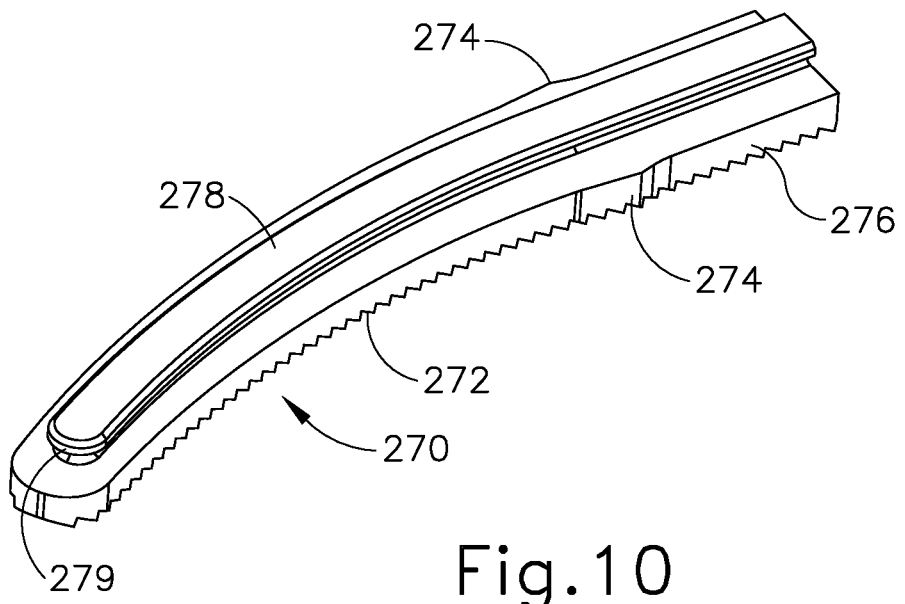
FIG. 10 depicts a top perspective view of the clamp pad of the end effector of FIG. 7, with the clamp pad in a curved form.
Figure 11:
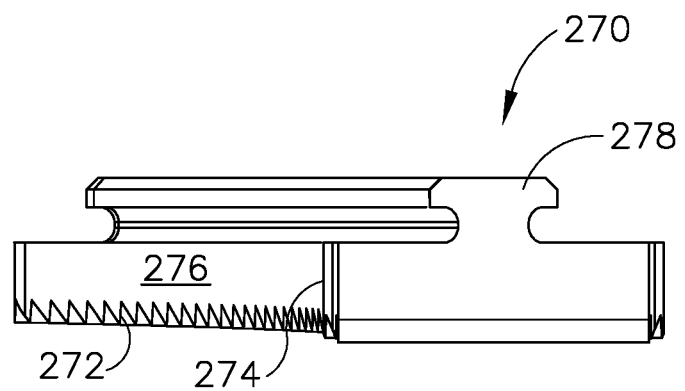
FIG. 11 depicts a proximal end view of the clamp pad of FIG. 10, with the clamp pad in a curved form.
Figure 12:
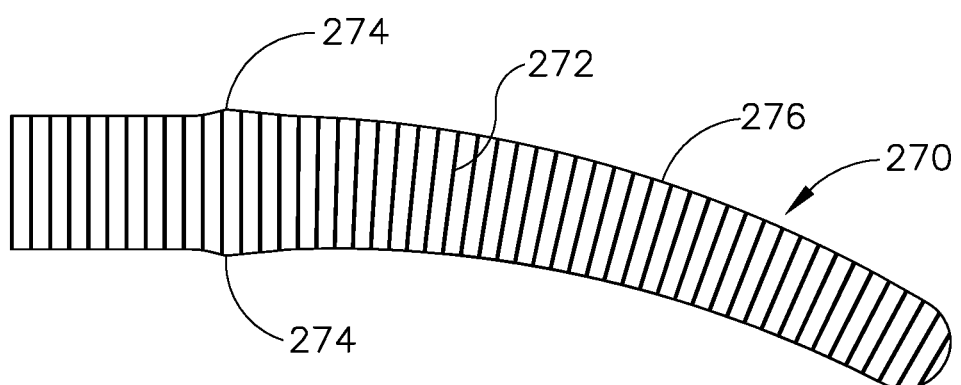
FIG. 12 depicts a bottom plan view of the clamp pad of FIG. 10, with the clamp pad in a curved form.

FIGS. 10-12 show how clamp pad (270) includes a plurality of teeth (272) along the underside of clamp pad (270) and a tenon (278) extending along an opposite top surface of clamp pad (270). Clamp pad (270) further comprises side surfaces (276) with projections (274) extending laterally outward from a longitudinal axis defined by clamp pad (270). Clamp pad (270) is comprised of a resilient material in this example. The resiliency of clamp pad (270) allows for projections (274) to deform inwardly when a force is applied against them as will be discussed further below. In the illustrated version, clamp pad (270) is shown as having a curved shape. In the present example this curved shape is pre-formed with the fabrication of clamp pad (270). In other versions, clamp pad (270) may be pre-formed with a straight configuration during fabrication; yet be flexible to assume a curved shape, for example when installed on a curved clamp arm (250) as will be described further below.

Figure 13:
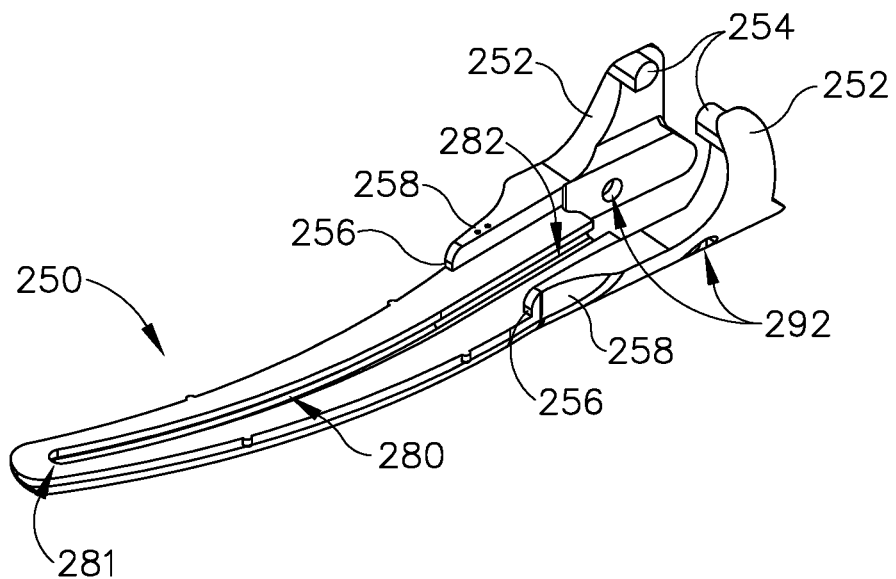
FIG. 13 depicts a bottom perspective view of the clamp arm of the end effector of FIG. 7.
Figure 14:
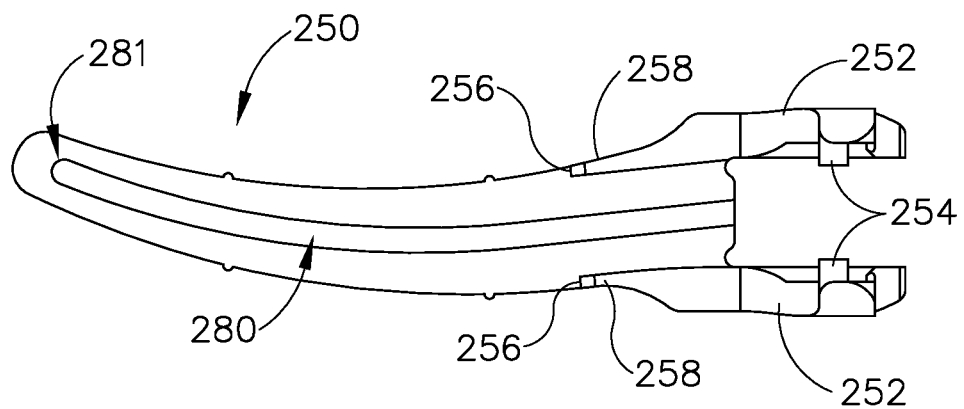
FIG. 14 depicts a bottom plan view of the clamp arm of FIG. 13.
Figure 15A:
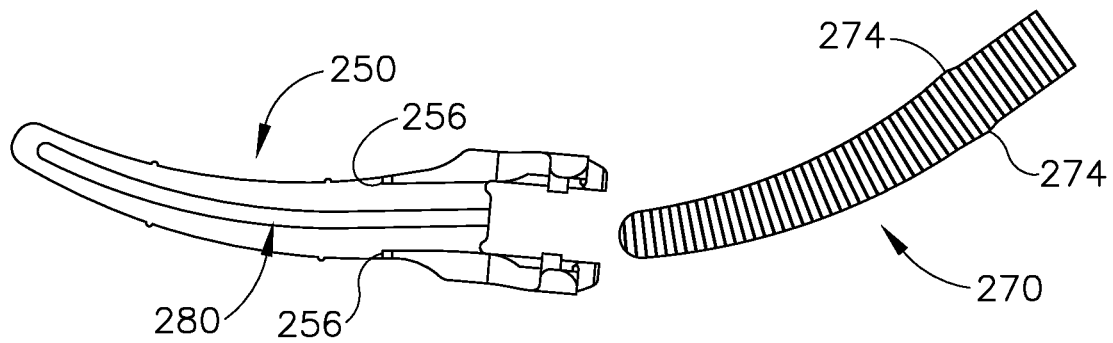
FIG. 15A depicts a bottom plan view of the clamp arm and clamp pad of the end effector of FIG. 7, with the clamp pad separated from the clamp arm.
Figure 15B:
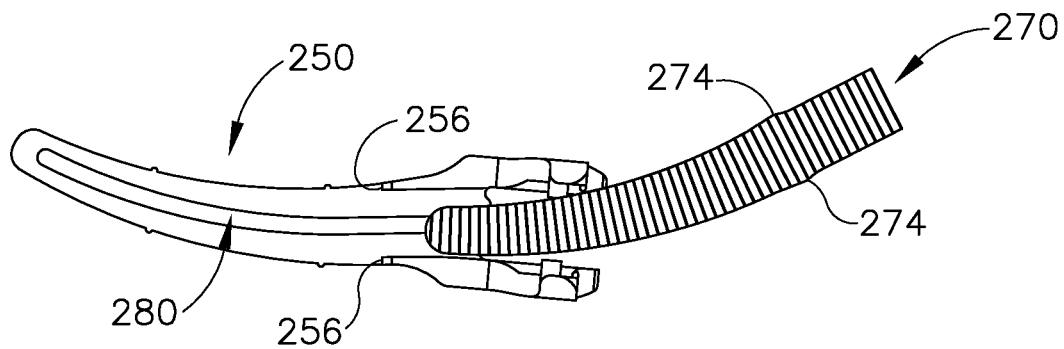
FIG. 15B depicts a bottom plan view of the clamp arm and clamp pad of FIG. 15A, with the clamp pad partially engaged with the clamp arm.
Figure 15C:
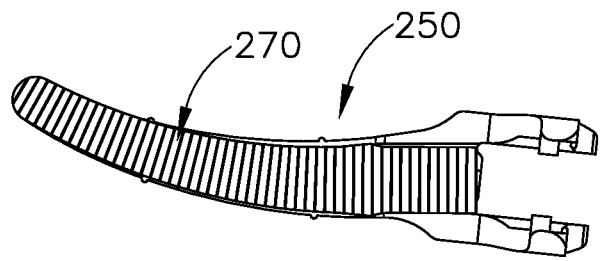
FIG. 15C depicts a bottom plan view of the clamp arm and clamp pad of FIG. 15B, with the clamp pad fully installed on the clamp arm.

FIGS. 13-14 show clamp arm (250) includes support gussets (258) on each side of clamp arm (250). Support gussets (258) include distal ends (256). Clamp arm (250) further includes mortise (280) along an underside of clamp arm (250). Mortise (280) is configured to complement tenon (278) of clamp pad (270) such that tenon (278) of clamp pad (270) slidably mates with mortise (280) of clamp arm (250) as best shown in FIGS. 15A-15C. In this respect, tenon (278) is configured to slide within mortise (280). In the illustrated version, mortise (280) and tenon (278) have complementary "T" shapes, where tenon (278) has a "T" shaped cross section as best seen in FIG. 11 and where mortise (280) is formed as a "T" shaped slot. In other versions, other complementary shapes other than "T" shape that may be used will be apparent to those of ordinary skill in the art in view of the teachings herein. As will be discussed further below, while clamp arm (250) may be detached from the remainder of end effector (200) when installing clamp pad (270) to clamp arm (250), this detachment of clamp arm (250) from end effector (200) is not required in all versions when installing clamp pad (270).

FIGS. 15A-15C show a series of views illustrating installation of clamp pad (270) onto clamp arm (250). As seen in comparing FIG. 15A with FIG. 15B, to install clamp pad (270) onto clamp arm (250) the distal end of clamp pad (270) is aligned with the proximal end of clamp arm (250). With clamp pad (270) and clamp arm (250) aligned, a distal end (279) of tenon (278) is inserted into a proximal end (282) of mortise (280). Tenon (278) and mortise (280) have a sliding engagement as mentioned above. As shown in comparing FIG. 15B with FIG. 15C, clamp pad (270) is advanced further distally relative to clamp arm (250) until clamp pad (270) is reaches its fully installed position as shown in FIG. 15C. During the process of installing clamp pad (270), projections (274) of clamp pad (270) will contact support gussets (258) of clamp arm (250) because the width of clamp pad (270) at projections (274) is greater than the inside width between support gussets (258). In some versions, the width at projections (274) is 0.115 inches while the inside width between support gussets (258) is 0.105 inches. Of course these dimensions are not required and in other versions other suitable dimensions will be apparent to those of ordinary skill in the art in view of the teachings herein.

During the act of advancing clamp pad (270) distally relative to clamp arm (250), support gussets (258) will exert force onto projections (274) of clamp pad (270). This force causes projections (274) to deform inwardly such that clamp pad (270) can continue to advance distally relative to clamp arm (250) to its fully installed position. In the fully installed position, projections (274) of clamp pad (270) are positioned distal of support gussets (258) such that projections (274) are no longer subject to the inward force exerted upon projections (274) by support gussets (258). Thus, projections (274) are no longer deformed inwardly toward the longitudinal axis defined by clamp pad (270). In this manner, clamp pad (270) is understood to have a snap-fit connection with clamp arm (250). Further, this snap-fit connection is selective, as clamp pad (270) is removable from clamp arm (250) as discussed below. Further yet, this snap-fit connection between clamp pad (270) and clamp arm (250) can be achieved without using adhesives, welds, or other mechanical fastening structures.

Support gussets (258) of clamp arm (250) include distal ends (256). With clamp pad (270) fully installed within clamp arm (250), distal ends (256) of support gussets (258) contact projections (274) and prevent clamp pad (270) from moving proximally relative to clamp arm (250). Furthermore, a closed distal end (281) of mortise (280) contacts distal end (279) of tenon (278) when clamp pad (270) is fully installed on clamp arm (250) such that clamp pad (270) is prevented from moving further distally relative to clamp arm (250). Based on the above description, is should be understood that closed distal end (281) of mortise (280) and distal ends (256) of support gussets (258) act as longitudinal stops. Although not required, in some versions, pin (290) may act to also prevent proximal movement of clamp pad (270) relative to clamp arm (250) once clamp pad (270) has been installed onto clamp arm (250).

After a surgical procedure, clamp pad (270) may be removed from clamp arm (250), and a new clamp pad with similar qualities can be installed if so desired. To remove clamp pad (270), clamp pad (270) is advanced proximally relative to clamp arm (250) with sufficient force such that projections (274) are deformed by contact with support gussets (258). With projections (274) deformed, clamp pad (270) can slide proximally past support gussets (258) such that clamp pad (270) is removable from clamp arm (250). In some examples, a user may grasp clamp pad (270) at or near projections (274) and apply a force to projections (274) to deform projections (274) inwardly while advancing clamp pad (270) proximally relative to clamp arm (250).

In some versions, clamp arm (250) may first be detached from inner tube (220) and outer sheath (210) prior to removing clamp pad (270) as described above. In detaching clamp arm (250), pivot pin (290) is removed and studs (254) are removed from openings (214) to decouple clamp arm (250) from inner tube (220) and outer sheath (210). In such examples where clamp arm (250) is detached from inner tube (220) and outer sheath (210) to either remove a used clamp pad (270) and/or install a new clamp pad (270), once clamp pad (270) is installed onto clamp arm (250), clamp arm assembly (240) may be coupled to inner tube (220) via pivot pin (290) and coupled to outer sheath (210) via studs (254) and openings (214). By way of example only, end effector (200) may be further constructed and operable in accordance with at least some of the teachings of U.S. Pat. No. 7,544,200, entitled "Combination Tissue Pad for Use with an Ultrasonic Surgical Instrument," issued Jun. 9, 2009, the disclosure of which is incorporated by reference herein.

By way of further example, and not limitation, in some versions clamp pad (270) may be about 0.760 inches in length in its straight formation. At its proximal end, clamp pad (270) may have a width of about 0.105 inches. About 0.590 inches from its distal end, clamp pad (270) may be its widest at a width of about 0.115 inches. Furthermore this widest part coincides with the width at projections (274). At about 0.540 inches from its distal end, clamp pad (270) may return in width to about 0.105 inches. As mentioned above, in some instances the width between the closest portions of support gussets (258) may be about 0.105 inches. Thus, in some examples the widest portion of clamp pad (270) is about 10% wider than the width between the closest portions of support gussets (258) of clamp arm (250). It should be understood that these dimensions are exemplary only and not required. Furthermore, in view of the teachings herein, other suitable dimensions will be apparent to those of ordinary skill in the art.

It should also be understood that a modified version of clamp pad (270) may be used as a retainer in versions where a clamp pad similar to clamp pad (58a) is used with clamp arm (250). In other words, clamp pad (58b) may be modified to include features similar to projections (274) in order to secure both clamp pads (58a, 58b) relative to clamp arm (250). Similarly, while clamp pad (270) is of a single unitary construction, clamp pad (270) may instead be formed as two or more pieces (e.g., that are aligned with each other longitudinally), with one or more of such pieces including features like projections (274). Such pieces of multi-piece versions of clamp pad (270) may be formed of different materials such that one piece of clamp pad (270) is formed of one material while another piece of clamp pad (270) is formed of another material. Moreover, the clamp pad retention configurations described herein may be used to provide additional space to accommodate tissue contacting pad material to interface with blade (79, 230), thereby enabling a longer cut length than conventional end effector configurations.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic instrument comprising: (a) a body; (b) a shaft assembly, wherein the shaft assembly extends distally from the body; (c) an acoustic waveguide positioned within the shaft assembly, wherein the waveguide is configured to acoustically couple with an ultrasonic transducer; and (d) an end effector, wherein the end effector comprises: (i) an ultrasonic blade in acoustic communication with the waveguide, and (ii) a clamp arm assembly, wherein the clamp arm assembly comprises: (A) a clamp arm pivotally coupled with the shaft assembly, and (B) a clamp pad configured to removably couple with the clamp arm using a snap-fit connection.

Example 2

The ultrasonic instrument of Example 1, wherein the clamp pad is configured to removably couple with the clamp arm while the clamp arm is pivotally coupled to the shaft assembly.

Example 3

The ultrasonic instrument of any one or more of Examples 1 through 2, wherein the clamp pad is configured to removably couple with the clamp arm while the clamp arm is decoupled from the shaft assembly.

Example 4

The ultrasonic instrument of any one or more of Examples 1 through 3, wherein the clamp arm comprises a pair of support gussets on each side of the clamp arm.

Example 5

The ultrasonic instrument of any one or more of Examples 1 through 4, wherein the clamp pad comprises a tenon extending longitudinally along the clamp pad.

Example 6

The ultrasonic instrument of Example 5, wherein the tenon extends along a top surface of the clamp pad.

Example 7

The ultrasonic instrument of any one or more of Examples 5 through 6, wherein the tenon comprises a cross sectional profile having a "T" shape.

Example 8

The ultrasonic instrument of any one or more of Examples 1 through 7, wherein the clamp pad comprises at least one projection extending outwardly from a longitudinal axis of the clamp pad.

Example 9

The ultrasonic instrument of Example 8, wherein the clamp pad comprises a pair of projections.

Example 10

The ultrasonic instrument of any one or more of Examples 8 through 9, wherein the clamp pad has a largest width at a location coinciding with the at least one projection.

Example 11

The ultrasonic instrument of any one or more of Examples 1 through 10, wherein the clamp arm comprises a mortise extending longitudinally along the clamp arm and configured to receive the clamp pad.

Example 12

The ultrasonic instrument of Example 11, wherein the mortise is formed as a "T" shaped slot.

Example 13

The ultrasonic instrument of any one or more of Examples 1 through 12, wherein the clamp arm comprises at least one support gusset configured to support the clamp pad.

Example 14

The ultrasonic instrument of any one or more of Examples 1 through 13, wherein the clamp arm comprises a pair of support gussets.

Example 15

The ultrasonic instrument of Example 14, wherein a first width between the pair of support gussets is less than a second width of the clamp pad.

Example 16

The ultrasonic instrument of any one or more of Examples 1 through 15, wherein the clamp pad comprises at least one projection, wherein the clamp pad has a first width at a location coinciding with the at least one projection, wherein the clamp arm comprises a pair of support gussets configured to support the clamp pad, wherein the clamp arm comprises a second width between the pair of support gussets, wherein the second width is less than the first width at the location coinciding with the at least one projection.

Example 17

The ultrasonic instrument of Example 16, wherein the first width is about 10% greater than the second width.

Example 18

A removable clamp arm assembly for use with an ultrasonic instrument having a shaft assembly extending distally from a body of the ultrasonic instrument, wherein the clamp arm assembly comprises: (a) a clamp arm selectively connectable with the shaft assembly, wherein the clamp arm comprises: (i) a first pivotable connection with the shaft assembly, (ii) a second pivotable connection with the shaft assembly, (iii) a mortise extending longitudinally along the clamp arm, and (iv) a pair of support gussets; and (c) a clamp pad selectively connectable with the clamp arm, wherein the clamp pad comprises: (i) a tenon extending along a top surface of the clamp pad, wherein the tenon is configured to slidably engage with the mortise, and (ii) at least one projection extending outwardly from a longitudinal axis of the clamp pad, wherein the at least one projection is configured to deform when contacting a select one of the pair of support gussets.

Example 19

The clamp arm assembly of Example 18, wherein the mortise is curved and wherein the clamp pad is flexible such that the clamp pad is configured to assume a curved shape when the tenon of the clamp pad is slidably engaged with the mortise.

Example 20

A method of assembling a clamp pad with a clamp arm of an ultrasonic surgical instrument, the method comprising the method steps of: (a) aligning a distal end of the clamp pad with a proximal end of the clamp arm; (b) inserting a distal end of a tenon in the clamp pad into a proximal end of a mortise in the clamp arm; (c) advancing the clamp pad distally relative to the clamp arm to slidably engage the tenon with the mortise; (d) positioning a projection of the clamp pad in contact with a support gusset of the clamp arm causing inward deformation of the projection; and (e) positioning the projection of the clamp pad distally of the support gusset of the clamp arm to remove the deformation of the projection caused by the projection contacting the support gusset.

VI. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The invention claimed is:

1. An ultrasonic instrument comprising:
   (a) a shaft assembly;
   (b) an acoustic waveguide positioned within the shaft assembly, wherein the waveguide is configured to acoustically couple with an ultrasonic transducer; and
   (c) an end effector, wherein the end effector comprises:
      (i) an ultrasonic blade in acoustic communication with the waveguide, and
      (ii) a clamp arm assembly, wherein the clamp arm assembly comprises:
         (A) a clamp arm pivotally coupled with the shaft assembly, and
         (B) a clamp pad defining a longitudinal axis in a longitudinal direction that bisects the clamp pad in a transverse direction and extends to a distal pad end, wherein the clamp pad has a first side surface extending proximally away from the distal pad end toward a first projection, wherein the first side surface has a proximal portion and a distal portion thereof, wherein the first projection transversely and outwardly extends beyond the proximal and distal portions of the first side surface in the transverse direction from the longitudinal axis such that the first projection is configured to removably couple with the clamp arm using a snap-fit connection,
      wherein the first projection is positioned longitudinally between the proximal portion of the first side surface and the distal portion of the first side surface.

2. The ultrasonic instrument of claim 1, wherein the clamp pad is configured to removably couple with the clamp arm while the clamp arm is pivotally coupled to the shaft assembly.

3. The ultrasonic instrument of claim 1, wherein the clamp pad is configured to removably couple with the clamp arm while the clamp arm is decoupled from the shaft assembly.

4. The ultrasonic instrument of claim 1, wherein the clamp arm comprises a pair of support gussets on each side of the clamp arm such that the pair of support gussets are positioned transversely opposite from each other, and wherein at least one of the pair of support gussets is configured to receive the first projection thereagainst and inwardly deform the first projection until the first projection resiliently outwardly returns to a snapped engagement with the at least one support gusset to form the snap-fit connection therebetween.

5. The ultrasonic instrument of claim 1, wherein the clamp pad comprises a pad body and a tenon, and wherein the tenon extends longitudinally along the pad body.

6. The ultrasonic instrument of claim 5, wherein the tenon extends along a top surface of the pad body, and wherein the first side surface and the first projection are positioned on the pad body.

7. The ultrasonic instrument of claim 6, wherein the tenon comprises a cross sectional profile having a "T" shape.

8. The ultrasonic instrument of claim 1, wherein the clamp pad has a second side surface extending proximally away from the distal pad end toward a second projection such that the second side surface is positioned transversely opposite from the first side surface, wherein the second projection transversely and outwardly extends beyond the second side surface in the transverse direction from the longitudinal axis such that the second projection is configured to removably couple with the clamp arm using the snap-fit connection.

9. The ultrasonic instrument of claim 8, wherein the second projection is positioned transversely opposite from the first projection such that the clamp pad has a largest transverse width at a location coinciding with the first and second projections.

10. The ultrasonic instrument of claim 1, wherein the clamp arm comprises a mortise extending longitudinally along the clamp arm and configured to receive the clamp pad.

11. The ultrasonic instrument of claim 1, wherein the clamp arm includes a first support gusset configured to receive the first projection thereagainst and inwardly deform the first projection until the first projection resiliently outwardly returns to a snapped engagement with the first support gusset to form the snap-fit connection therebetween.

12. The ultrasonic instrument of claim 11, wherein the clamp arm further includes a second support gusset positioned transversely opposite from the first support gusset.

13. The ultrasonic instrument of claim 12, wherein the first support gusset and the second support gusset define a first transverse width therebetween, wherein the clamp pad at the first projection defines a second transverse width therealong, and wherein the first transverse width is less than the second transverse width.

14. The ultrasonic instrument of claim 13, wherein the clamp pad has a second side surface extending proximally away from the distal pad end toward a second projection such that the second side surface is positioned transversely opposite from the first side surface, wherein the second projection transversely and outwardly extends beyond the second side surface in the transverse direction from the longitudinal axis such that the second projection is configured to removably couple with the clamp arm using the snap-fit connection, and wherein the clamp pad at the first projection defines the second transverse width therealong from the first projection to the second projection.

15. The ultrasonic instrument of claim 14, wherein the first transverse width is about 10% greater than the second transverse width.

16. The ultrasonic instrument of claim 1, wherein the proximal portion of the first side surface tapers transversely inward toward the distal pad end.

17. A method of assembling a clamp pad with a clamp arm of an ultrasonic surgical instrument, the method comprising the method steps of:
   (a) aligning a distal end of the clamp pad with a proximal end of the clamp arm;
   (b) inserting a distal end of a tenon in the clamp pad into a proximal end of a mortise in the clamp arm;
   (c) advancing the clamp pad distally relative to the clamp arm to slidably engage the tenon with the mortise;
   (d) positioning a projection of the clamp pad in contact with a first support gusset of the clamp arm causing inward deformation of the projection toward a second support gusset of the clamp arm such that the projection is compressed between the first and second gussets; and
   (e) positioning the projection of the clamp pad distally of the first and second support gussets of the clamp arm to remove the deformation of the projection caused by the projection being compressed between the first and second support gussets.

18. An ultrasonic instrument comprising:
   (a) a shaft assembly;
   (b) an acoustic waveguide positioned within the shaft assembly, wherein the waveguide is configured to acoustically couple with an ultrasonic transducer; and
   (c) an end effector, wherein the end effector comprises:
      (i) an ultrasonic blade in acoustic communication with the waveguide, and
      (ii) a clamp arm assembly, wherein the clamp arm assembly comprises:
         (A) a clamp arm pivotally coupled with the shaft assembly, and
         (B) a clamp pad including a pad body and a tenon and defining a longitudinal axis in a longitudinal direction that bisects the clamp pad in a transverse direction and extends to a distal pad end, wherein the clamp pad has a first side surface extending proximally away from the distal pad end toward a first projection, wherein the first projection transversely and outwardly extends beyond the first side surface in the transverse direction from the longitudinal axis such that the first projection is configured to removably couple with the clamp arm using a snap-fit connection,
      wherein the tenon extends longitudinally along the pad body and comprises a cross sectional profile having a "T" shape.

19. The ultrasonic instrument of claim 18, wherein the tenon extends along a top surface of the pad body, and wherein the first side surface and the first projection are positioned on the pad body.

* * * * *